United States Patent
Horzewski et al.

(10) Patent No.: US 6,325,823 B1
(45) Date of Patent: *Dec. 4, 2001

(54) ENDOVASCULAR PROSTHESIS ACCOMMODATING TORSIONAL AND LONGITUDINAL DISPLACEMENTS AND METHODS OF USE

(75) Inventors: Michael J. Horzewski, San Jose, CA (US); Gerald Dorros, Scottsdale, AZ (US)

(73) Assignee: Revasc Corporation, San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/430,589

(22) Filed: Oct. 29, 1999

(51) Int. Cl.$^7$ .................................................. A61F 2/06
(52) U.S. Cl. ............................................................ 623/1.16
(58) Field of Search ..................................... 623/1.16, 1.13, 623/1.15; 606/191, 195, 198, 108, 194

(56) References Cited

U.S. PATENT DOCUMENTS

| | | | |
|---|---|---|---|
| 4,655,771 | 4/1987 | Wallsten | 623/1 |
| 4,850,999 | 7/1989 | Planck | 623/1 |
| 5,078,726 | 1/1992 | Kreamer | 606/194 |
| 5,084,065 | 1/1992 | Weldon et al. | 623/1 |
| 5,163,951 | 11/1992 | Pinchuk et al. | 623/1 |
| 5,211,658 | 5/1993 | Clouse | 623/1 |
| 5,219,355 | 6/1993 | Parodi et al. | 606/191 |
| 5,275,622 | 1/1994 | Lazarus | 623/1 |
| 5,314,444 | 5/1994 | Gianturco | 606/195 |
| 5,354,329 | 10/1994 | Whalen | 623/1 |
| 5,383,892 * | 1/1995 | Cardon et al. | 606/198 |
| 5,413,597 | 5/1995 | Krajicek | 623/1 |
| 5,413,598 | 5/1995 | Moreland | 623/1 |
| 5,562,727 | 10/1996 | Turk et al. | 623/1 |
| 5,628,788 | 5/1997 | Pinchuk | 623/1 |
| 5,629,077 | 5/1997 | Turnlund et al. | 442/38 |
| 5,632,772 | 5/1997 | Alcime et al. | 623/1.35 |
| 5,639,278 | 6/1997 | Dereume et al. | 623/1.35 |
| 5,651,174 | 7/1997 | Schwartz et al. | 29/527.2 |
| 5,653,746 | 8/1997 | Schmitt | 623/1 |
| 5,669,924 | 9/1997 | Shaknovich | 606/108 |
| 5,674,277 | 10/1997 | Freitag | 623/1 |
| 5,674,576 | 10/1997 | Anderson et al. | 623/1 |
| 5,683,449 | 11/1997 | Marcade | 623/1 |
| 5,697,970 | 12/1997 | Schmitt et al. | 623/1 |
| 5,720,735 | 2/1998 | Dorros | 604/284 |
| 5,755,772 | 5/1998 | Evans et al. | 623/1 |
| 5,755,773 | 5/1998 | Evans et al. | 623/1 |
| 5,755,777 | 5/1998 | Chuter | 623/1 |

(List continued on next page.)

OTHER PUBLICATIONS

Carlos E. Ruiz et al., "A Novel Method for Treatment of Abdominal Aortic Aneurysms Using Percutaneous Implantation of a Newly Designed Endovascular Device", *Circulation*, 91:2470–2477, 1995.

Carlos E. Ruiz et al., "Percutaneous Treatment of Abdominal Aortic Aneurysm in a Swine Model", *Circulation*, 96:2438–2448, 1997.

*Primary Examiner*—Kevin Truong
(74) *Attorney, Agent, or Firm*—Fish & Neave; Nicola A. Pisano

(57) ABSTRACT

A prosthesis is provided comprising a plurality of telescoping tubular members that are deployed and assembled in vivo to define a lumen through a diseased portion of a vascular system. The individual tubular members are capable of accommodating torsional and longitudinal displacements caused by relative motion of the healthy portions on either side of the diseased portion of vessel.

20 Claims, 3 Drawing Sheets

U.S. PATENT DOCUMENTS

| | | | |
|---|---|---|---|
| 5,758,562 | 6/1998 | Thompson | 87/33 |
| 5,759,174 | 6/1998 | Fischell et al. | 604/96 |
| 5,788,626 | 8/1998 | Thompson | 600/36 |
| 5,800,507 | 9/1998 | Schwartz | 623/1 |
| 5,824,040 | 10/1998 | Cox et al. | 623/1 |
| 5,824,052 | 10/1998 | Khosravi et al. | 623/1 |
| 5,868,783 * | 2/1999 | Tower | 623/1.16 |
| 5,902,332 * | 5/1999 | Schatz | 623/1.16 |
| 5,921,995 | 7/1999 | Kleshinski | 606/153 |
| 5,961,548 | 10/1999 | Shmulewitz | 623/1 |
| 6,001,125 | 12/1999 | Golds et al. | 623/1 |

* cited by examiner

ENDOVASCULAR PROSTHESIS ACCOMMODATING TORSIONAL AND LONGITUDINAL DISPLACEMENTS AND METHODS OF USE

FIELD OF THE INVENTION

The field of the invention relates to prostheses for repairing occlusive and aneurysmal vascular disease, and more particularly, an endovascular prosthesis capable of accommodating torsional and longitudinal displacements between its ends.

BACKGROUND OF THE INVENTION

The recent introduction of endoluminal graft prostheses, such as stents and stent-graft systems, for the treatment of arterial and venous defects, such as aneurysms, hold the promise of reduced procedural morbidity and mortality compared to previously known surgical alternatives.

For example, U.S. Pat. No. 5,078,726 to Kreamer describes a stent graft system wherein a graft is affixed to intact portions of a vessel above and below an aneurysm using coiled sheet stents. Likewise, U.S. Pat. No. 5,219,355 to Parodi et al. shows a graft affixed to intact portions of a vessel wall above and below an aneurysm using balloon-expandable stents. U.S. Pat. No. 5,275,622 to Lazarus also shows a graft affixed at its upper and lower ends using self-expanding sinusoidal rings.

One drawback encountered with systems such as those described in the foregoing patents is that relative movement of the upper and lower fixation devices after initial deployment of the stents may result in twisting of the graft material. Such torsional displacements between the ends of the graft may cause a reduction in the flow area of the graft and/or the creation of stagnation zones that promote clotting within the lumen of the graft.

In addition, excluding an aneurysm from the flow path and subsequent clotting of the blood contained within the aneurysmal cavity may result in foreshortening of the vessel, thereby causing longitudinal movement of the graft fixation devices towards one another. Such longitudinal displacements may in turn cause buckling: the graft may bow outward, sag, kink, or crumple, again promoting stagnation zones and thrombus formation within the lumen of the graft.

Moreover, because the structure of the human vascular tree varies from patient to patient, each procedure is a unique experience. For example, an aneurysm existing in a straight vessel segment may be excluded with a tubular graft, whereas an aneurysm occurring at, abutting or including a vessel bifurcation may require the use of a custom prosthesis.

Repair of an aneurysm located adjacent to a bifurcated vessel presents further technical difficulties, including the inability to easily enter both vessel branches because of vessel size, vessel tortuosity, device size, or limited device flexibility. There may also be an inability to adequately expand the device and create fluid seals at the ends of the aneurysm. If a custom device does not fit, surgical intervention also may be necessary to remove the device, thereby exposing the patient to additional risk. These problems are compounded where the diseased area of a vessel may change in length, size, and shape after the prosthesis has been deployed.

In view of the foregoing, it would be desirable to provide a vascular prosthesis that may be readily adapted to vessels of various sizes, including bifurcated vessels.

It further would be desirable to provide a vascular prosthesis that can accommodate changes in the size and shape of the vessel after the prosthesis has been deployed.

It also would be desirable to provide a vascular prosthesis that can accommodate torsional and longitudinal displacements between the fixation devices that affix the vascular prosthesis to intact portions of the vessel wall, without twisting or kinking of the prosthesis.

SUMMARY OF THE INVENTION

In view of the foregoing, it is an object of the present invention to provide a vascular prosthesis that may be readily adapted to vessels of various sizes, including bifurcated vessels.

It is another object of this invention to provide a vascular prosthesis that can accommodate changes in the size and shape of the vessel after the prosthesis has been deployed.

It is a further object of the present invention to provide a vascular prosthesis that can accommodate torsional and longitudinal displacements between the fixation devices that affix the vascular prosthesis to intact portions of the vessel wall, without twisting or kinking of the prosthesis.

These and other objects of the invention are accomplished by providing a vascular prosthesis having first and second interconnecting members. One end of each of the first and second members is fixed to an intact portion of vessel wall on either side of a vascular defect to be excluded. In accordance with the principles of the present invention, the other ends of the first and second members are interconnected so that one end telescopes and rotates within the other end. The first and second members of the graft of the present invention therefore define a custom, self-adjusting member, assembled in vivo, that spans a diseased section of a vascular system.

The prosthesis of the present invention also facilitates repair of complex vascular structures, such as bifurcated vessels. Changes in the size and shape of the damaged section may be readily accommodated without buckling or twisting of the graft. In addition, the prosthesis may comprise a semipermeable material that relieves pressure build up in the aneurysm cavity, and promotes clot formation in the aneurysm cavity.

BRIEF DESCRIPTION OF THE DRAWINGS

Further features of the invention, its nature and various advantages will be more apparent from the accompanying drawings and the following detailed description of the preferred embodiments in which.

DETAILED DESCRIPTION OF THE PREFERRED EMBODIMENTS

The present invention provides an endovascular prosthesis capable of accommodating torsional and longitudinal displacements between its ends. The two portions of the prosthesis define a custom, self-adjusting device that may be assembled in vivo to span a diseased section of a vessel. The prosthesis is especially well suited for repairing complex vascular structures, such as bifurcated vessels. Changes in the size and shape of the damaged section are accommodated without twisting, kinking or buckling of the prosthesis.

Figure 1:
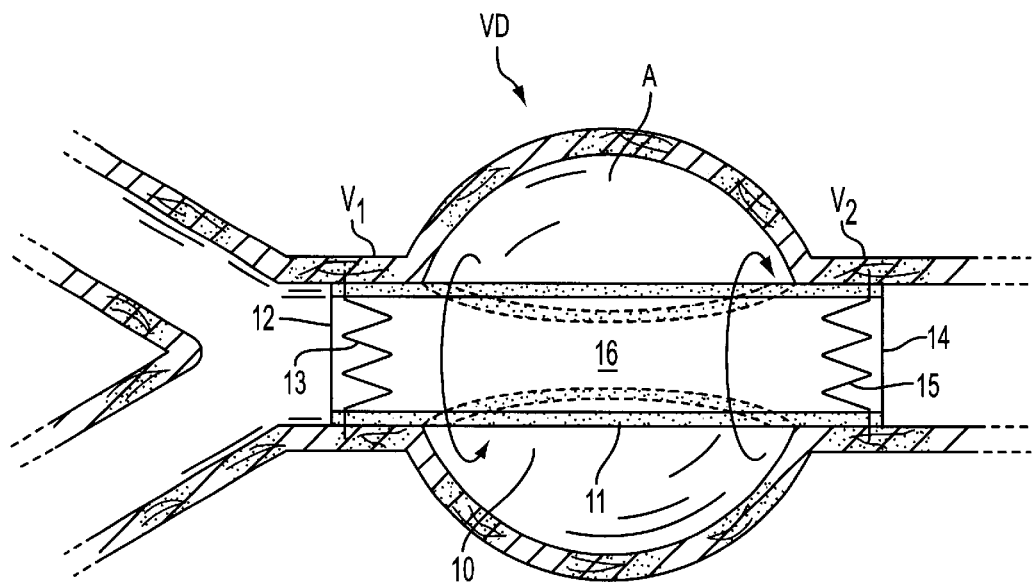
FIG. 1 is a side sectional view of a previously known prosthesis subjected to a torsional displacement of the aneurysmal cavity.

Referring to FIG. 1, a previously known prosthesis 10 is described that spans a vascular defect, illustratively an aneurysm. Prosthesis 10 may comprise any of the stent-graft combinations described hereinabove. Prosthesis 10 comprises graft 11 having end 12 affixed by stent 13 to portion $V_1$ of the vessel, and end 14 affixed by stent 15 to portion $V_2$ of the vessel. Prosthesis 10 includes central lumen 16 that conducts blood from portion $V_1$ of the vessel to portion $V_2$, while excluding vascular defect VD.

Vascular defect VD may be, for example, a localized, pathological, blood filled dilation of vessel V caused by a disease or weakening of the vessel wall to form aneurysm A. Though vascular defect VD is illustratively described herein as an aneurysm, the defect may also be an obstruction, stenosis, dissection, clot, weakened vessel wall or the like without departing from the scope of the present invention.

As a consequence of deployment of prosthesis 10, vessel V is subjected to a twisting moment T that creates a relative torsional displacement of ends 12 and 14 of the prosthesis, for example, by clotting of the blood excluded within the aneurysm or return of the vessel portions $V_1$ and $V_2$ to an original state before the development of vascular defect VD. This torsional displacement may lead to twisting of the material constituting graft 11, and result in reduced flow area of central lumen 16 (shown in dotted line in FIG. 1). In addition, the helical folds of material in graft 11 accompanying twisting of graft 11 may create stagnation zones within central lumen 16 that promote clot and thrombus formation within lumen 16 of prosthesis 10. Accordingly, central lumen 16 may become a site that spawns emboli, or may even completely occlude. It is an object of the present invention to remedy this defect in previously known stent-graft systems.

Figure 2:
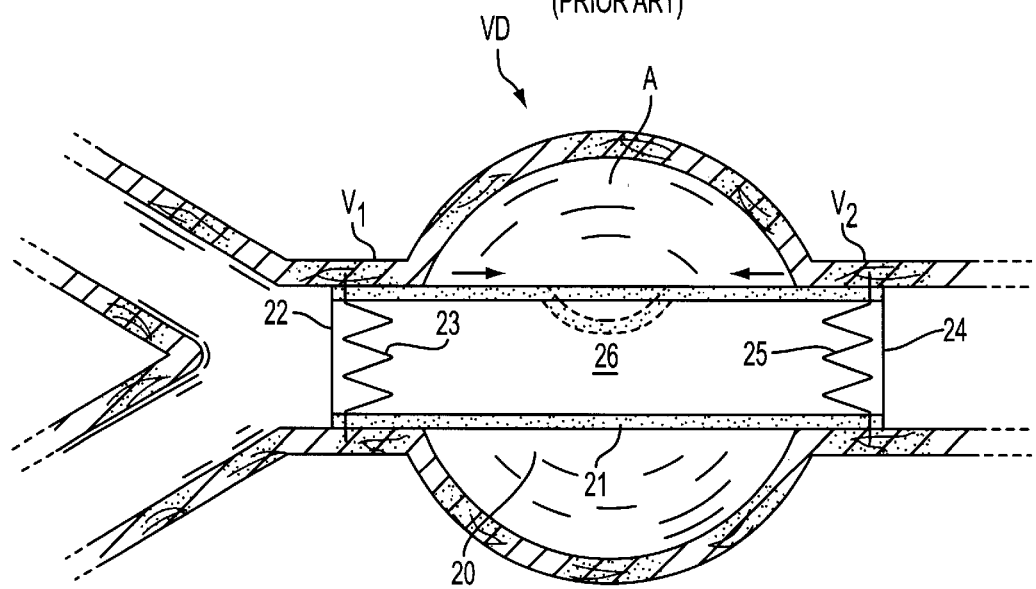
FIG. 2 is a side sectional view of a previously known prosthesis subjected to a longitudinal reduction in the size of the aneurysmal cavity.

Referring now also to FIG. 2, problems associated with longitudinal foreshortening of previously known stent-graft systems are also described. Prosthesis 20 comprises graft 21 having end 22 affixed by stent 23 to vessel portion $V_1$ and end 24 affixed by stent 25 to vessel portion $V_2$. Prosthesis 20 includes central lumen 26 that channels blood between vessel portions $V_1$ and $V_2$, while excluding vascular defect VD, illustratively aneurysm A.

It is contemplated that after successful exclusion of aneurysm A, clotting of the blood captured within the aneurysm may result in shortening of the diseased length of vessel V between vessel portions $V_1$ and $V_2$, thereby applying a compressive axial load to graft 21 of prosthesis 20. This compressive axial load may in turn cause longitudinal movement of ends 22 and 24 of prosthesis 20 towards one another. Such longitudinal displacement is expected to cause buckling of graft 21 (shown in dotted line in FIG. 2), resulting in sagging or crumpling of the graft material in a such a way that central lumen 26 of the prosthesis is narrowed. Narrowing of central lumen 26 also may promote the development of stagnation zones and thrombus formation sites within central lumen 26 of prosthesis 20.

Alternatively, an axial tensile load may be applied to opposite ends 22 and 24 of prosthesis 20, also resulting in reduction of the flow area within central lumen 26. It is also an object of the present invention to address this drawback of previously known stent-graft systems.

Figure 3A:
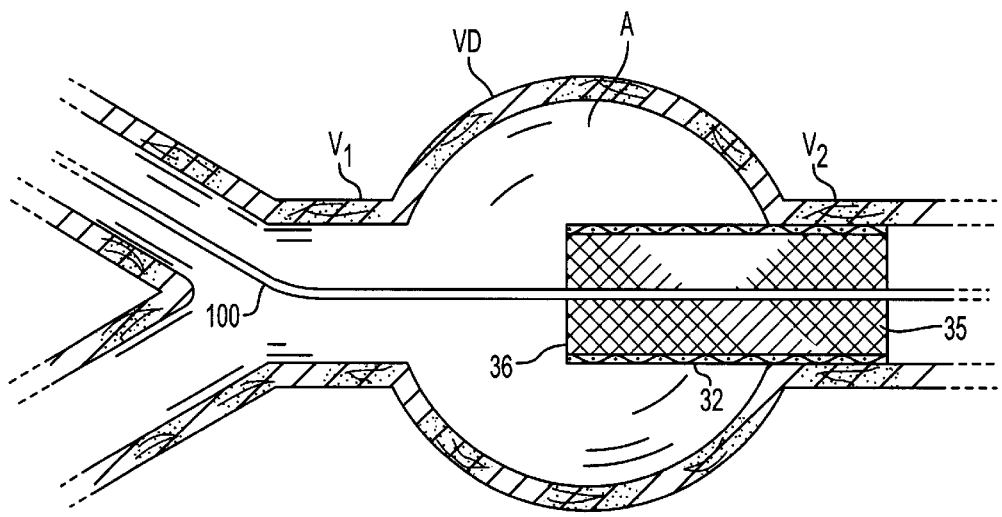
FIGS. 3A and 3B are side sectional views of an embodiment of the endovascular prosthesis of the present invention formed by interconnecting graft members.
Figure 3B:
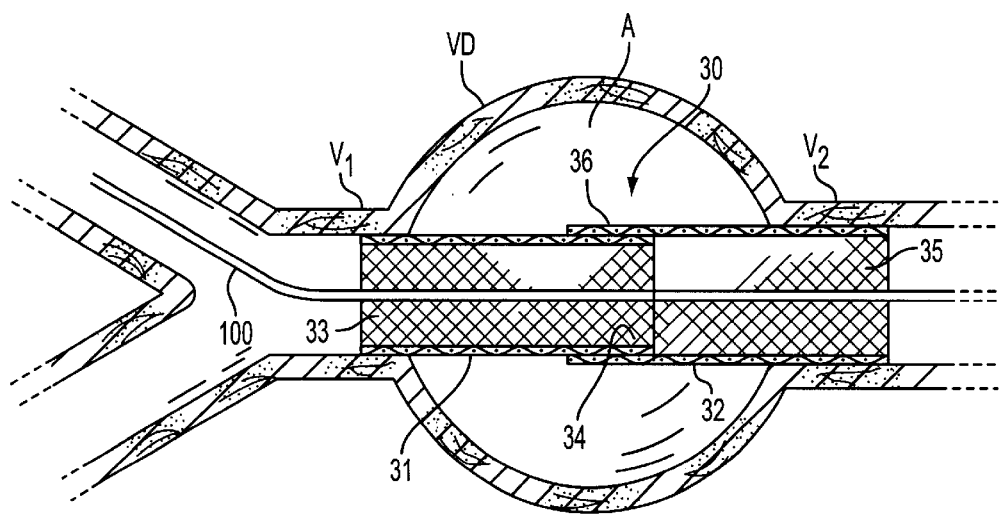

Referring now to FIGS. 3A and 3B, the steps of assembling in vivo an endovascular prosthesis 30, constructed in accordance with the principles of the present invention, is described. Prosthesis 30 comprises interconnecting tubular members 31 and 32 disposed within vascular defect VD, illustratively aneurysm A. Tubular member 31 has end 33 affixed to vessel portion $V_1$ and free end 34. Tubular member 32 has end 35 affixed to vessel portion $V_2$ and free end 36. In accordance with the present invention, free ends 34 and 36 of tubular members 31 and 32, respectively, are interconnected in an overlapping, telescoping manner within aneurysm A to provide a structurally rigid prosthesis that replaces the weakened walls of the vessel.

Tubular members 31 and 32, which may comprise a polymer covered plastically deformable alloy or metal structure, are expanded to engage the interior wall of non-diseased vessel portions $V_1$ and $V_2$ and preferably may be customized to fit the diameter of vessel V. Free ends 34 and 36 are interconnected so that the may move longitudinally relative to one another and rotate relative to one another. Prosthesis 30 therefore may be customized to accommodate the length of the aneurysm by varying the extent to which tubular members 31 and 32 overlap one another. Since the length and radial orientation of tubular members 31 and 32 may be determined upon deployment within the vessel, prosthesis 30 may be customized in vivo to vascular defects of varying sizes and shapes.

As described hereinabove, one problem associated with repairing a diseased area of a vessel with a fixed-length prosthesis is that the diseased blood vessel may shrink or expand in length, or otherwise change in shape. The change in size or shape of the diseased vessel may cause the prosthesis to become kinked or twisted, thereby narrowing or blocking the lumen through the diseased area formed by the prosthesis. Because tubular members 31 and 32 of prosthesis 30 may move axially and radially with respect to each other once deployed, prosthesis 30 can accommodate changes in the size and shape of the vessel.

More specifically, in FIG. 3A, vascular defect VD may be a localized pathological, blood filled dilation of blood vessel V caused by a disease or weakening of the blood vessel wall to form aneurysm A. Tubular member 32 is introduced into vessel portion $V_2$ (illustratively, the descending aorta) transluminally along guide wire 100 via a femoral artery, as is per se known. Tubular member 32 then is expanded so that end 35 engages healthy vessel portion $V_2$ and free end 36 extending within aneurysm A as shown in FIG. 3A. Thus, tubular member 32 is secured in place only by its attachment to vessel portion $V_2$.

Assembly of prosthesis 30 is now completed by introducing tubular member 31 into vessel V along guide wire 100, so that free end 34 is disposed within free end 36 of tubular member 32. Tubular member 31 is then expanded, so that end 33 engages vessel portion $V_1$ and the interconnected tubular members 31 and 32 exclude aneurysm A from the blood flow path. Free end 34 of tubular member 31, which is overlapped by, and thus interconnected with free end 36 of tubular member 32, permits rotational and longitudinal motion between the tubular members, while minimizing blood passing through the overlap region into aneurysm A. Prosthesis 30 thus forms a continuous lumen through aneurysm A.

The length of prosthesis 30 is determined by the length of free end 34 of tubular member 31 that overlaps free end 36 of tubular member 32. Prosthesis 30 may therefore be customized in vivo to fit within vessel defects of various sizes. Once tubular members 31 and 32 have been deployed, they may move radially and axially with respect to each other to accommodate torsional or longitudinal movement of vessel portions $V_1$ and $V_2$. For example, tubular member 31 may rotate without causing free end 36 of tubular member 32 to rotate. In addition, tubular member 31 may telescope within tubular member 32 if vascular defect VD shrinks in length. Thus, if vascular defect VD changes in size or shape, prosthesis 30 can adapt without becoming kinked or twisted, as is believed to occur with prostheses 10 and 20 of FIGS. 1 and 2.

Preferably, tubular members 31 and 32 comprise a semi-permeable or impermeable material, such as a nickel-titaniums alloy ("nitinol"), stainless steel, or polymeric mesh, that provides a structural framework for prosthesis 30, while providing sufficient flexibility to allow the placement of the device within a vascular defect. In the preferred embodiment shown in FIGS. 3A and 3B, tubular members 31 and 32 comprise a mesh having a plurality of longitudinal members interconnected by serpentine members inclined at an angle with respect to the longitudinal members, such as described in U.S. Pat. Nos. 5,314,444 and 5,758,562, which are incorporated herein by reference.

Figure 4:
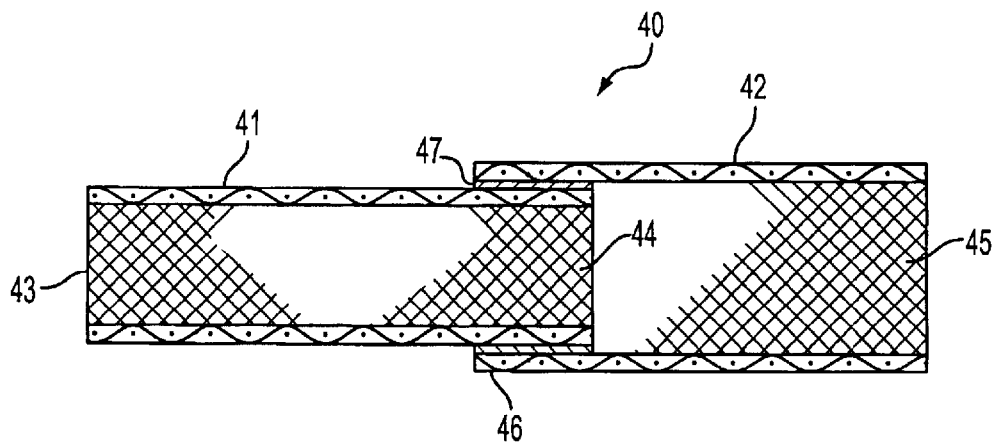
FIG. 4 is a side sectional view of an alternative embodiment of the prosthesis of the present invention including a slidable seal disposed between the interconnecting graft members.

Referring now to FIG. 4, an alternative embodiment of a prosthesis of the present invention is described. Prosthesis 40 is similar in construction to prosthesis 30 of FIG. 3, but in addition includes a resilient seal that couples the free ends of the tubular members together.

In particular, prosthesis 40 comprises interconnected tubular members 41 and 42. Tubular member 41 includes end 43 adapted to expand to engage a healthy vessel portion, such as vessel portion $V_1$ in FIG. 3, and free end 44. Tubular member 42 includes end 45 adapted to expand to engage a healthy vessel portion, such as vessel portion $V_2$ in FIG. 3, and free end 46, which overlaps free end 44 of tubular member 41 when the prosthesis is fully assembled.

In the embodiment of FIG. 4, tubular member 41 further includes resilient seal 47 affixed to either the exterior surface of free end 44 or the interior surface of free end 46. Resilient seal 47 Preferably comprises an annular cylindrical gasket of soft material such as polytetrafluoroethylene ("PTFE") or biocompatible closed-cell foam. Seal 47 is designed to reduce bypass flow of blood through the overlapping free ends into the vascular defect VD, while reducing friction between overlapping ends 44 and 46 to facilitate the movement and rotation of tubular members 41 and 42 with respect to each other.

Figure 5:
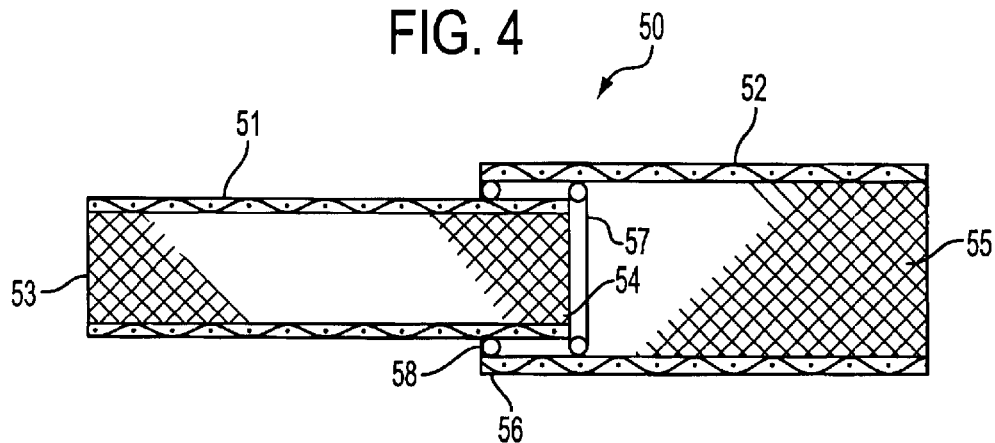
FIG. 5 is a side sectional view of another alternative embodiment of the prosthesis of the present invention.

With respect to FIG. 5, a further alternative embodiment is described. Prosthesis 50 comprises tubular member 51 having tissue-engaging end 53 and free end 54, and tubular member 52 having tissue-engaging end 55 and free end 56. Free end 56 overlaps free end 54 of tubular member 51 when the prosthesis assembled. Rings 57 and 58 prevent tubular members 51 and 52 from coming apart once deployed in the diseased vessel. Tubular member 51 has ring 57 attached to free end 54, while tubular member 52 has 58 attached to free end 56. Rings 57 and 58 are expandable along with tubular members 51 and 52 when the tubular members are deployed in the vessel.

Specifically, ring 57 is placed inside tubular member 52 when tubular member 51 is positioned inside the vessel to sealingly engage the interior wall of tubular member 52. When tubular member 51 moves proximally (to the left in FIG. 5), ring 57 engages ring 58 to prevent further proximal movement. Thus, rings 57 and 58 prevent tubular members 51 and 52 from becoming separated. In addition, rings 57 and 58 allow tubular members 51 and 52 to move axially and radially with respect to each other without compromising the prosthesis or the vessel.

Figure 6:
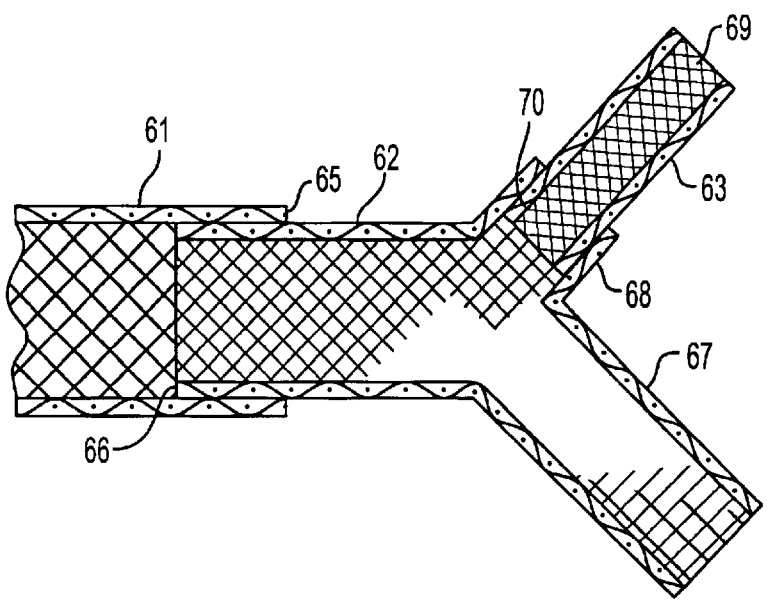
FIG. 6 is a side sectional view of a further alternative embodiment of the prosthesis of the present invention suitable for use in bifurcated vessels.

The principles of the present invention also may be applied to grafts for use in bifurcated vessels, for example, so that a second tubular member may span a vessel bifurcation. With respect to FIG. 6, prosthesis 60 is described comprises three telescoping portions 61, 62 and 63 that are assembled in vivo. Tubular member 61 has a tissue-engaging end (not shown) adapted to engage a healthy vessel portion, as in FIG. 3, and free end 65. Tubular member 62 includes trunk end 66 that telescopes within free end 65 of tubular 25 member 61, branch 67 and joining region 68. Tubular member 63 includes tissue-engaging end 69 and free end 70. When fully assembled, trunk end 66 of tubular member 62 is overlappingly interconnected with free end 65 of tubular member 61, and free end 70 of tubular member 63 is overlappingly interconnected with joining region 68 of tubular member 62.

In accordance with the principles of the present invention, tubular members 61, 62 and 63 are axially and radially movable with respect to each other. If either of the branches of the vessel move with respect to each other or the trunk of the vessel, tubular members 61, 62 and 63 can move and rotate with respect to each to accommodate the changes in relative orientation of the vessels, without buckling or twisting of one or both legs of prosthesis 60. The prosthesis of FIG. may be especially advantageous in implementing bifurcated grafts, such as that described in U.S. Pat. No. 5,961,548 to Shmulewitz, which is incorporated herein by reference.

Tubular members 61–63 preferably comprise balloon expandable metal or metal alloy structures, such as described in the above-incorporated patents, and are covered with an impermeable or semi-permeable biocompatible membrane. Alternatively, tubular members 61–63 may comprise membrane covered self-expanding structures or thermally-expanded metal alloy structures. Tubular members 61–63 may incorporate any of the sealing mechanisms described hereinabove, such as resilient seal 47 of the embodiment of FIG. 4 or the rings of the embodiment of FIG. 5.

While preferred illustrative embodiments of the present invention are described above, it will be apparent to one skilled in the art that various changes and modifications may be made therein without departing from the invention. Although, the present invention has been described with respect to vascular defects, the present invention also may be used to reline an organ. The foregoing references to a vessel should therefore be understood to include organs. In is intended in the appended claims to cover all such changes and modifications which fall within the true spirit and scope of the invention.

What is claimed is:

1. A prosthesis for repairing a diseased vessel comprising:
    a first tubular member having tissue-engaging end adapted to engage an interior wall of a first healthy section of vessel and free end, and a lumen extending therebetween the tissue-engaging end and the free end; and
    a second tubular member separate from the first tubular member, having a tissue-engaging end adapted to engage an interior wall of a second healthy section of vessel and a free end, and a lumen extending therebetween the tissue-engaging end and the free end, the free end of the second tubular member adapted to receive the free end of the first tubular member in telescoping relation, wherein the free end of the first tubular member moves independently of the free end of the second tubular member when longitudinal and torsional loads are applied to the first tubular member.

2. The prosthesis of claim 1 wherein the first and second tubular members are individually deployed in vivo.

3. The prosthesis of claim 1 wherein one of the free ends of the first and second tubular members further comprises a resilient seal.

4. The prosthesis of claim 3 wherein the resilient seal comprises an annular cylindrical gasket.

5. The prosthesis of claim 1 wherein a first ring is attached to the free end of the first tubular member and a second ring is attached to the free end of the second tubular member.

6. The prosthesis of claim 1 wherein at least one of the first and second tubular members expands from a contracted configuration to an expanded configuration.

7. The prosthesis of claim 6 wherein one of the first and second tubular members is balloon expandable.

8. The prosthesis of claim 6 wherein one of the first and second tubular members is self-expanding.

9. The prosthesis of claim 6 wherein one of the first and second tubular members is thermally expanded.

10. The prosthesis of claim 1 wherein the second tubular member includes first and second branches, the tissue-engaging end of the second tubular member is disposed on the first branch and the second branch includes a branch free end, and the prosthesis further comprises a third tubular member having a tissue-engaging end and a free end, the branch free end of the second tubular member adapted to received the free end of the third tubular member.

11. A prosthesis for repairing a diseased vessel comprising:

a first tubular member having tissue-engaging end adapted to engage an interior wall of a first healthy section of vessel and free end, and a lumen extending therebetween the tissue-engaging end and the free end; and a second tubular member, separate from the first tubular member, having a tissue-engaging end adapted to engage an interior wall of a second healthy section of vessel and a free end, and a lumen extending therebetween the tissue-engaging end and the free end, the free end of the second tubular member adapted to receive the free end of the first tubular member in telescoping relation, wherein the free end of the first tubular member moves independently of the free end of the second tubular member when torsional loads are applied to the first tubular member.

12. The prosthesis of claim 11 wherein one of the free ends of the first and second tubular members further comprises a resilient seal.

13. The prosthesis of claim 11 wherein at least one of the first and second tubular members expands from a contracted configuration to an expanded configuration.

14. The prosthesis of claim 11 wherein the second tubular member includes first and second branches, the tissue-engaging end of the second tubular member is disposed on the first branch and the second branch includes a branch free end, and the prosthesis further comprises a third tubular member having a tissue-engaging end and a free end, the branch free end of the second tubular member adapted to received the free end of the third tubular member.

15. A method of repairing a diseased portion of a vessel comprising:

providing a first tubular member having tissue-engaging end, and free end, and a lumen extending therebetween; and providing a second tubular member having tissue-engaging end and free end, and a lumen extending therebetween;

transluminally advancing the first tubular member to a first position within a vessel;

deploying the first tubular member so that the tissue-engaging end engages a healthy portion of the vessel and the free end extends within the diseased portion of the vessel;

transluminally advancing the second tubular member to a second position within a vessel;

deploying the second tubular member so that the tissue-engaging end engages a healthy portion of the vessel and the free end is received within the free end of the first tubular member so that longitudinal and torsional motion of the free end of the first tubular member is not transmitted to the free end of the second tubular member.

16. The method of claim 15 wherein the second tubular member is deployed so that the free end of the second tubular member telescopes within the free end of the first tubular member.

17. The method of claim 15 wherein one of the free ends of the first and second tubular members further comprises a resilient seal, the method further comprising sealing the free end of the first tubular member to the free end of the second tubular member to reduce bypass flow.

18. The method of claim 15 wherein the first tubular member expands from a contracted configuration to an expanded configuration, deploying the first tubular member comprises expanding the first tubular member from the contracted configuration to the expanded configuration.

19. The method of claim 15 wherein deploying the first tubular member comprises applying a radially outwardly directed force to the tissue-engaging end of the first tubular member.

20. The method of claim 15 wherein deploying the first tubular member comprises removing a compressive force to permit the tissue-engaging end of the first tubular member to self-expand.

* * * * *